US008100961B2

(12) United States Patent
Vyavahare et al.

(10) Patent No.: US 8,100,961 B2
(45) Date of Patent: Jan. 24, 2012

(54) ELASTIN STABILIZATION OF CONNECTIVE TISSUE

(75) Inventors: Narendra R. Vyavahare, Easley, SC (US); Jason C. Isenburg, Pendleton, SC (US); Dan T. Simionescu, Central, SC (US)

(73) Assignee: Clemson University Research Foundation (CURF), Clemson, SC (US)

( * ) Notice: Subject to any disclaimer, the term of this patent is extended or adjusted under 35 U.S.C. 154(b) by 0 days.

(21) Appl. No.: 12/748,849

(22) Filed: Mar. 29, 2010

(65) Prior Publication Data

US 2010/0185272 A1 Jul. 22, 2010

Related U.S. Application Data

(63) Continuation of application No. 11/827,121, filed on Jul. 10, 2007, now Pat. No. 7,713,543, which is a continuation of application No. 11/387,454, filed on Mar. 23, 2006, now Pat. No. 7,252,834.

(60) Provisional application No. 60/674,631, filed on Apr. 25, 2005.

(51) Int. Cl.
*A61F 2/82* (2006.01)
*C07H 15/203* (2006.01)
*A61M 29/00* (2006.01)

(52) U.S. Cl. ...... 623/1.13; 623/1.42; 606/194; 536/18.2
(58) Field of Classification Search .................. None
See application file for complete search history.

(56) References Cited

U.S. PATENT DOCUMENTS

| | | | |
|---|---|---|---|
| 2,987,446 A | 6/1961 | Riethmuller | |
| 4,992,264 A | 2/1991 | Diot et al. | |
| 5,015,677 A | 5/1991 | Benedict et al. | |
| 5,019,400 A | 5/1991 | Gombotz et al. | |
| 5,081,157 A | 1/1992 | Pomerantz | |
| 5,252,344 A | 10/1993 | Shi | |
| 5,512,291 A | 4/1996 | Li | |
| 5,720,950 A | 2/1998 | Poiani et al. | |
| 5,750,150 A | 5/1998 | Okazaki et al. | |
| 5,834,449 A | 11/1998 | Thompson et al. | |
| 5,876,744 A | 3/1999 | Della Valle et al. | |
| 5,916,597 A | 6/1999 | Lee et al. | |
| 5,922,253 A | 7/1999 | Herbert et al. | |
| 5,955,097 A | 9/1999 | Tapolsky et al. | |
| 5,968,500 A | 10/1999 | Robinson | |
| 5,972,999 A | 10/1999 | Murad | |
| 6,063,770 A | 5/2000 | Falcon | |
| 6,071,541 A | 6/2000 | Murad | |
| 6,146,616 A | 11/2000 | Msika et al. | |
| 6,228,387 B1 | 5/2001 | Borod | |
| 6,235,294 B1 | 5/2001 | Perrier et al. | |
| 6,239,114 B1 | 5/2001 | Guthrie et al. | |
| 6,254,898 B1 | 7/2001 | Bragaglia | |
| 6,258,122 B1 | 7/2001 | Tweden et al. | |
| 6,290,949 B1 * | 9/2001 | French et al. | 424/93.2 |
| 6,432,922 B1 | 8/2002 | Brunck et al. | |
| 6,437,004 B1 | 8/2002 | Perricone | |
| 6,444,234 B1 | 9/2002 | Kirby et al. | |
| 6,463,317 B1 | 10/2002 | Kucharczyk et al. | |
| 6,469,053 B1 | 10/2002 | Romanczyk, Jr. et al. | |
| 6,471,723 B1 | 10/2002 | Ashworth et al. | |
| 6,471,973 B1 | 10/2002 | Perrier et al. | |
| 6,517,824 B1 | 2/2003 | Kohn et al. | |
| 6,531,154 B1 | 3/2003 | Mathiowitz et al. | |
| 6,576,613 B1 | 6/2003 | Brunck et al. | |
| 6,586,405 B2 | 7/2003 | Semple et al. | |
| 6,610,320 B2 | 8/2003 | Schmitz et al. | |
| 6,630,163 B1 | 10/2003 | Murad | |
| 6,676,977 B2 | 1/2004 | Murad | |
| 6,747,059 B1 | 6/2004 | Romanczyk, Jr. et al. | |
| 6,773,704 B1 | 8/2004 | Chapman et al. | |
| 6,787,152 B2 | 9/2004 | Kirby et al. | |
| 6,800,292 B1 | 10/2004 | Murad | |
| 6,830,577 B2 | 12/2004 | Nash et al. | |
| 6,867,188 B2 | 3/2005 | Qvist et al. | |
| 6,927,205 B2 | 8/2005 | Patt | |
| 6,927,206 B2 | 8/2005 | Patt | |
| 6,929,626 B2 | 8/2005 | DiCarlo et al. | |

(Continued)

FOREIGN PATENT DOCUMENTS

EP 0617964 A1 10/1994

(Continued)

OTHER PUBLICATIONS

Abstract—Ammoury et al., "Jejunal absorption, pharmacological activity, and pharmacokinetic evaluation of indomethacin-loaded poly(d,l-lactide) and poly(isobutylcyanoacrylate) nanocapsules in rats," Pharm Res 1991;8 (1):101-105. BASF Corporation, Pluronic(R) F127 Block Copolymer Surfactant Technical Bulletin, 2002.
Berge et al., "Pharmaceutical Salts," Journal of Pharmaceutical Sciences, 66(1): 1-19 (1977).
Blonder et al., "Dose-Dependent Hyperlipidemia in Rabbits Following Administration of Poloxamer 407 Gel," Life Sciences vol. 65, No. 21, pp. PL 261-PL 266, 1999.
Brem et al., "Interstitial chemotherapy with drug polymer implants for the treatment of recurrent gliomas," J. Neurosurgery, 1991;74(3): 441-446.
Bu et al., "IKKβ-dependent NF-κB pathway controls vascular inflammation and intimal hyperplasia," The FASEB Journal express article 10.1096/fj.04-2645fje.,published online Jun. 6, 2005.
Calvo et al., "Long-circulating PEGylated polycyanoacrylate nanoparticles as new drug carrier for brain delivery," Pharm Res 2001;18(8):1157-1166.

(Continued)

*Primary Examiner* — Shanon A Foley
(74) *Attorney, Agent, or Firm* — Dardi & Herbert, PLLC; Peter S. Dardi; Mengmeng Fahrni

(57) ABSTRACT

A method and product are provided for the treatment of connective tissue weakened due to destruction of tissue architecture, and in particular due to elastin degradation. The treatment agents employ certain unique properties of phenolic compounds to develop a protocol for reducing elastin degradation, such as that occurring during aneurysm formation in vasculature. According to the invention, elastin can be stabilized in vivo and destruction of connective tissue, such as that leading to life-threatening aneurysms in vasculature, can be tempered or halted all together. The treatment agents can be delivered or administered acutely or chronically according to various delivery methods, including sustained release methods incorporating perivascular or endovascular patches, use of microsphere carriers, hydrogels, or osmotic pumps.

13 Claims, 7 Drawing Sheets

U.S. PATENT DOCUMENTS

| | | | |
|---|---|---|---|
| 6,979,347 | B1 | 12/2005 | Wu et al. |
| 7,008,411 | B1 | 3/2006 | Mandrusov et al. |
| 7,182,744 | B2 | 2/2007 | Yamasaki et al. |
| 7,208,179 | B1 | 4/2007 | Drohan et al. |
| 7,252,834 | B2 | 8/2007 | Vyavahare et al. |
| 7,323,169 | B2 | 1/2008 | Goldenberg et al. |
| 7,371,257 | B2 * | 5/2008 | Sahatjian et al. ............ 623/1.46 |
| 7,491,188 | B2 | 2/2009 | Holman et al. |
| 7,713,543 | B2 | 5/2010 | Vyavahare et al. |
| 2001/0029349 | A1 | 10/2001 | Leschinsky |
| 2003/0078659 | A1 | 4/2003 | Yang |
| 2003/0170287 | A1 | 9/2003 | Prescott |
| 2003/0171287 | A1 | 9/2003 | Morishita et al. |
| 2003/0228364 | A1 | 12/2003 | Nathan |
| 2003/0232895 | A1 * | 12/2003 | Omidian et al. ................ 521/99 |
| 2004/0153145 | A1 | 8/2004 | Simionescu et al. |
| 2004/0158320 | A1 | 8/2004 | Simionescu et al. |
| 2004/0181252 | A1 | 9/2004 | Boyle et al. |
| 2005/0079202 | A1 | 4/2005 | Chen et al. |
| 2005/0245893 | A1 | 11/2005 | Leschinsky |
| 2006/0034925 | A1 | 2/2006 | Au et al. |
| 2007/0212386 | A1 | 9/2007 | Patravale et al. |
| 2007/0212387 | A1 | 9/2007 | Patravale et al. |
| 2007/0282422 | A1 | 12/2007 | Biggs et al. |
| 2007/0293937 | A1 | 12/2007 | Biggs et al. |
| 2008/0255510 | A1 | 10/2008 | Wang |
| 2009/0105686 | A1 | 4/2009 | Snow et al. |
| 2009/0186370 | A1 | 7/2009 | Ogle et al. |
| 2009/0214654 | A1 | 8/2009 | Isenburg et al. |
| 2009/0258049 | A1 | 10/2009 | Klein et al. |
| 2010/0016833 | A1 | 1/2010 | Ogle et al. |
| 2010/0119605 | A1 | 5/2010 | Isenburg et al. |
| 2010/0189876 | A1 | 7/2010 | Kokish et al. |
| 2010/0209472 | A1 | 8/2010 | Wang |
| 2010/0292641 | A1 | 11/2010 | Wijay et al. |

FOREIGN PATENT DOCUMENTS

| | | |
|---|---|---|
| GB | 2057437 A | 4/1981 |
| WO | 01/21228 A1 | 3/2001 |
| WO | 01/41735 A2 | 6/2001 |
| WO | 2004/047620 A2 | 6/2004 |
| WO | 2007/064152 A1 | 6/2007 |
| WO | 2007/133479 A2 | 11/2007 |
| WO | 2009/036118 A1 | 3/2009 |
| WO | 2009/061787 A1 | 5/2009 |
| WO | 2010/026578 A1 | 3/2010 |
| WO | 2010/027735 A2 | 3/2010 |
| WO | 2010/080575 A2 | 7/2010 |
| WO | 2010/120620 A1 | 10/2010 |
| WO | 2010/140163 A2 | 12/2010 |

OTHER PUBLICATIONS

Connolly et al., "Tryglicidimine crosslinking of porcine aortic valve cusps or bovine pericardium results in improved biocompatibility, biomechanics and calcification resistance," Am J Pathol 2005;166(1):1-13.

Daugherty et al., "Mouse models of abdominal aortic aneurysms," Arterioscler. Thromb. Vasc. Biol. 2004;24(3):429-434.

Dawson et al., "Pharmacotherapy of abdominal aortic aneurysms," Curr Vasc Pharmacol, 2006;4(2):129-149.

Freestone et al., "Influence of Hypercholesterolemia and Adventitial Inflammation on the Development of Aortic Aneurysm in Rabbits," Arterioscler. Thromb. Vasc. Biol. 1997;17:10-17.

Freestone et al., "Inflammation and Matrix Metalloproteinases in the Enlarging Abdominal Aortic Aneurysm," Arterioscler. Thromb. Vasc. Biol. 1995;15:1145-1151.

Gertz et al., "Aneurysm of the rabbit common carotid artery induced by periarterial application of calcium chloride in vivo," J. Clin. Invest., 1988;81:649-656.

Hagerman et al. eds. "Antinutrients and Phytochemicals in Foods" (Methods for determination of condensed and hydrolysable tannins), Washington D.C. American Chemical Society, 1997, pp. 209-222.

Harvard Health Publications, "Hemorrhoids and what to do about them," http://www.revolutionhealth.com/conditions/digestive/hemmorrhoids/introduction/what-to-do, Aug. 21, 2006.

Houghton et al., "Elastin fragments drive disease progression in a murine model of emphysema," J. Clin. Invest. 2006;116(3): 753-759 (2006).

Isenburg et al., "Elastin stabilization for treatment of abdominal aortic aneurysms," Circulation 2007;115 (13):1729-1737.

Isenburg et al., "Structural requirements for stabilization of vascular elastin by polyphenolic tannins," Biomaterials, 2006;27:3645-3651.

Isenburg et al., "Tannic acid treatment enhances biostability and reduces calcification of glutaraldehyde fixed aortic wall," Biomaterials, 2005;26:1237-1245.

Isenburg et al., "Elastin stabilization in cardiovascular implants: Improved resistance to enzymatic degredation by treatment with tannic acid," Biomaterials, 2004;25:3293-3302.

Jayakrishnan et al., "Glutaraldehyde as a fixative in bioprostheses and drug delivery matrices," Biomaterials Mar. 1996; 17(5):471-84.

Jorge-Herrero et al, "Calcification of pericardial tissue pretreated with different amino acids," Biomaterials 1996;17(6): 571-575.

Kasyanov et al., "Tannic acid mimicking dendrimers as small intestine submucosa stabilizing nanomordants," Biomaterials, 2006;27:745-751.

Abstract—Luck et al., "Polyphenols, astringency and proline-rich proteins," Phytochemistry 1994;37(2):357-371.

Musumeci et al., "PLA/PLGA nanoparticles for sustained release of docetaxel," International Journal of Pharmaceutics 325 (2006) 172-179.

Prabha et al., "Critical determinants in PLGA/PLA nanoparticle-mediated gene expression," Pharm Res 2004;21(2):354-364.

Ross et al., "The elastic fiber. I. The separation and partial characterization of its macromolecular component," J Cell Biol 1969;40(2):366-381.

Abstract—Simionescu et al., "Lysine-enhanced glutaraldehyde croslinking of collagenous biomaterials," J Biomed Mater Res 1991;25(12):1495-1505.

Simionescu et al., "Galloylglucoses of low molecular weight as mordant in electron microscopy. I. Procedure, and evidence for mordanting effect," J Cell Biol 1976;70(3):608-621.

Abstract—Stacchino et al. "Detoxification process for glutaraldehyde-treated bovine pericardium: biological, chemical and mechanical characterization," J Heart Valve Dis. 1998;7(2):190-4.

Tambiah et al., "Provocation of Experimental Aortic Inflammation and Dilation by Inflammatory Mediators and Chlamydia Pneumoniae", British Journal of Surgery 2001, 88:935-940.

Vyavahare et al., "Elastin calcification and its prevention with aluminum chloride pretreatment," Am J Pathol 1999;155(3):973-982.

Search Report and Written Opinion for PCT/US0613090 dated Sep. 25, 2006.

Search Report and Opinion for EP06758289 dated Apr. 17, 2004.

* cited by examiner

ELASTIN STABILIZATION OF CONNECTIVE TISSUE

RELATED APPLICATIONS

The present application is a continuation of U.S. patent application Ser. No. 11/827,121 filed Jul. 10, 2007, now U.S. Pat. No. 7,713,543 entitled "Elastin Stabilization of Connective Tissue", incorporated herein by reference, which is a continuation of U.S. patent application Ser. No. 11/387,454, filed Mar. 23, 2006, now U.S. Pat. No. 7,252,834, incorporated herein by reference, which has a priority date based on Provisional Application Ser. No. 60/674,631, which was filed on Apr. 25, 2005.

FEDERALLY SPONSORED RESEARCH AND DEVELOPMENT

The United States Government may have rights to this invention pursuant to National Institutes of Health Grant No. HL-61652.

BACKGROUND OF THE INVENTION

One of the most common results of the degradation of vasculature is aneurysm. By definition, the term "aneurysm" is simply an abnormal widening or ballooning at the wall of a blood vessel. This condition can be devastating due to the potential for rupture or dissection that can lead to massive bleeding, stroke, or hemorrhagic shock, and can be fatal in an estimated 80% of cases. Aneurysms can be caused by any of a large class of degenerative diseases and pathologies including atherosclerotic disease, defects in arterial components, genetic susceptibilities, and high blood pressure, among others, and can develop silently over a period of years. The hallmarks of aneurysms include enzymatic degradation of vascular structural proteins such as elastin, inflammatory infiltrates, calcification, and eventual overall destruction of the vascular architecture. For example, FIG. 1 graphically illustrates the difference in elastin content between a healthy aorta and an aneurysmal aorta. As can be seen, elastin content of the damaged structure is 70% less than that of the healthy structure.

Current methods of treatment for diagnosed aneurysms are limited to invasive surgical techniques. After initial diagnosis of a small aneurysm, the most common medical approach is to follow up the development of the aneurysm and after reaching a pre-determined size (e.g., about 5 cm in diameter), surgical treatment is applied. Current surgical treatments are limited to either an endovascular stent graft repair or optionally complete replacement of the diseased vessel with a vascular graft. While such surgical treatments can save lives and improve quality of life for those suffering aneurysm, dangers beyond those of the surgery itself still exist for the patient due to possible post-surgery complications (e.g., neurological injuries, bleeding, or stroke) as well as device-related complications (e.g., thrombosis, leakage, or failure). Moreover, depending upon the location of the aneurysm, the danger of an invasive surgical procedure may outweigh the possible benefits of the procedure, for instance in the case of an aneurysm deep in the brain, leaving the sufferer with very little in the way of treatment options. Moreover, surgical treatments may not always provide a permanent solution, as vascular grafts can loosen and dislodge should the aneurysm progress following the corrective surgery.

Aneurysm is not the only condition for which enzymatic degradation of structural proteins is a hallmark. Other conditions in which structural protein degradation appears to play a key role include Marfan syndrome, supravalvular aortic stenosis, and chronic obstructive pulmonary disease (COPD). For those afflicted, such conditions lead to, at the very least, a lowered quality of life and often, premature death.

Phenolic compounds are a diverse group of materials that have been recognized for use in a wide variety of applications. For instance, they naturally occur in many plants, and are often a component of the human diet. Phenolic compounds have been examined in depth for efficacy as free radical scavengers and neutralizers, for instance in topical skin applications and in food supplements. Phenolic compounds are also believed to prevent cross-linking of cell membranes found in certain inflammatory conditions and are believed to affect the expressions of specific genes due to their modulation of free radicals and other oxidative species (see, e.g., U.S. Pat. No. 6,437,004 to Perricone).

What are needed in the art are treatment protocols and compositions for stabilization of the organs and tissues affected by degenerative conditions such as aneurysm. In particular, treatment protocols utilizing phenolic compounds could provide a safe, less invasive route for the stabilization of the structural architecture in order to temper growth and/or development of such conditions.

SUMMARY OF THE INVENTION

In one embodiment, the present invention is directed to a method for stabilizing connective tissue containing elastin. For instance, the method can include applying a phenolic compound directly to connective tissue. Phenolic compounds for use in the disclosed methods include a hydrophobic core and at least one phenolic group joined to the hydrophobic core.

In one preferred embodiment, the connective tissue targeted by the protocol can be a component of a blood vessel. For instance, the method can be utilized to treat arteries, and in one particular embodiment, the aorta.

Methods of the invention can include providing a phenolic compound in a suitable drug delivery vehicle such as, for example, a sustained release drug delivery vehicle. In one embodiment, a drug delivery vehicle, e.g., a microencapsulation, a hydrogel, an implantable device such as a stent, a patch, a vascular graft, or the like, can be located adjacent to the connective tissue for direct delivery of the phenolic compound to the tissue.

In other embodiments, other delivery methods and devices may be used. For instance, a composition including a phenolic compound and a parenterally acceptable carrier can be injected directly into the connective tissue. In yet another embodiment, the disclosed compounds can be delivered to the connective tissue of a blood vessel wall via intravenous delivery.

Methods and compositions described herein can be beneficially utilized in one embodiment for in vivo therapeutic or prophylactic treatments, and in one particular embodiment, for treatment of aneurysmal blood vessels.

The present invention is also directed to compositions that can be used in the methods. For instance, compositions of the invention can include between about 0.0001 w/v % and about 10 w/v % of a phenolic compound and a parenterally acceptable carrier. In general, the composition can have a pH between about 4 and about 9, for instance between about 5.5 and about 7.

In one preferred embodiment, the phenolic compound can be a tannin or a tannin derivative. For instance, the phenolic compound can be pentagalloylglucose.

BRIEF DESCRIPTION OF THE FIGURES

A full and enabling disclosure of the present invention, including the best mode thereof, to one of ordinary skill in the art, is set forth more particularly in the remainder of the specification, including reference to the accompanying drawings in which:

FIGS. 10B and 10C illustrate a control aorta and a treated aorta following Verhoeff van Giesson staining.

DETAILED DESCRIPTION OF THE INVENTION

Figure 1:
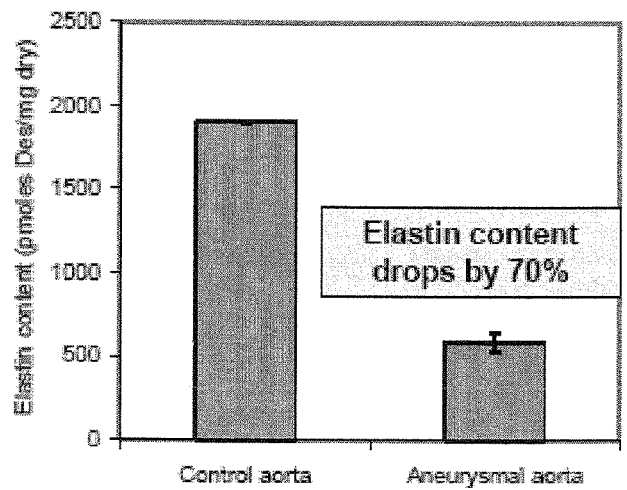
FIG. 1 is a graphical representation of the difference in elastin content of a healthy aorta and an aneurysmal aorta in an animal model.

Reference now will be made in detail to embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

The present invention is generally directed to methods and phenolic compounds that can be beneficially utilized for stabilization of connective tissue. In particular, the presently disclosed methods and compounds can stabilize the elastin component of connective tissue, and thereby prevent the degradation of the structural architecture of the connective tissue. For instance, the disclosed methods can be utilized to prevent the structural breakdown of organs incorporating the targeted connective tissue, e.g., blood vessels. In one particular embodiment, the materials and methods disclosed herein can be utilized in the treatment of chronic connective tissue degenerative conditions. For instance, the invention can be directed to in vivo treatment methods and compositions. Connective tissue targeted by the process can be stabilized so as to be less susceptible to protein degradation that can be brought about due to any of a variety of mechanisms and/or conditions including, for example, those associated with aneurysm, atherosclerotic disease, genetic susceptibilities, blunt force injury, Marfan's syndrome, and the like.

Connective tissue is the framework upon which the other types of tissue, i.e., epithelial, muscle, and nervous tissues, are supported. Connective tissue generally includes individual cells not directly attached to one another and held within the extracellular matrix. The extracellular matrix, in turn, includes the ground substance (e.g., the minerals of bone, the plasma of blood, etc.) and the fibrous component including collagen fibers and elastin fibers. Connective tissue can assume widely divergent architectures, ranging from blood, in which the fibrous component is absent and the ground substance is fluid, to dense connective tissue, which includes a relatively high proportion of extracellular fibers (e.g., collagen) and may contain little of the other connective tissue components. There are many specialized types of connective tissue, one example being elastic tissue, in which elastic fibers are the major component of the tissue and the amount of factors commonly found in other types of connective tissue, such as collagen and proteoglycans, may be minimal.

The compounds and processes disclosed herein are directed to stabilization of the elastin component of connective tissue, and in one particular embodiment, stabilization of the elastin component of vasculature. It should be understood that while the invention is directed in one particular embodiment to the stabilization of blood vessels susceptible to the formation of aneurysms, in other embodiments other organs, other diseases and/or other conditions can be treated. In particular, the disclosed treatment agents and treatment protocols are applicable to any animal or human connective tissue that include an elastin component.

Elastin is the protein constituent of connective tissue responsible for the elasticity and recoil of the tissue. Moreover, elastin is quite abundant in connective tissue. In fact, elastin is the most abundant extracellular matrix protein found in the aortic wall. Elastin polypeptide chains are naturally cross-linked together to form rubber-like, elastic fibers. Unlike collagen, elastin molecules can uncoil into a more extended conformation when the fiber is stretched and will recoil spontaneously as soon as the stretching force is relaxed. Elastin degeneration in connective tissue pathology is generally caused by enzymes including elastase enzymes and matrix metalloproteinase (MMP) enzymes that can be secreted by vascular cells as well as by infiltrating inflammatory cells. While many aspects of the methods and schemes of various enzymes leading to elastin degradation remain unknown, in general, it is believed that most enzymes attack and bind the protein at a site away from the crosslinks.

According to the present invention, degradation of connective tissue can be prevented or slowed through the stabilization of the elastin component of the tissue with a phenolic compound. In particular, it is believed that any of a number of natural and synthetic phenolic compounds can bind elastin and thereby protect elastin from degradation, for instance due to the action of elastin degrading enzymes. Accordingly, in one embodiment, the present invention is directed to methods and compounds that can inhibit enzyme-catalyzed degradation of elastin, and in particular elastase and/or MMP catalyzed degradation of elastin.

Phenolic compounds encompassed by the present invention include any compound that includes at least one phenolic group bound to a hydrophobic core. While not wishing to be bound by any particular theory, it is believed that interaction between the phenolic compound and elastin proteins include aspects involving both the hydroxyl group as well as the hydrophobic core of the molecules. In particular, it is believed that phenolic compounds can stabilize elastin proteins through both steric means and bond formation and thereby protect sites on the protein susceptible to enzyme-mediated (e.g., elastase or MMP-mediated) cleavage. Specifically, it is believed that hydroxyl groups of a phenolic compound can bind elastin multivalently, for instance via hydrogen bond formation with amino acid residues such as polar amino acid residues including methionine, glycine and proline, such that multiple proteins can interact with a single molecule to create a three-dimensional cross-link structure involving multiple elastin molecules. Moreover, in certain embodiments, the phenolic compounds of the present invention can include one or more double bonds, with which the phenolic compounds can covalently bind to the elastin, forming an even stronger and more permanent protective association between the phenolic compound and the elastin of the connective tissue. In addition, the large hydrophobic regions of the elastin protein, which are believed to contain sites susceptible to elastase-mediated cleavage, are also believed to contain sites of association between the hydrophobic core of the phenolic compound and the protein. Thus, the association between the phenolic compound and the protein molecules are believed to protect specific binding sites on the protein targeted by enzymes through the association of the protein with the hydrophobic core and can also sterically hinder the degradation of the protein through the development of the large three dimensional cross-link structure.

Phenolic compounds encompassed by the present invention include materials including a hydrophobic core and one or more phenol groups extending from the hydrophobic portion of the molecule. For instance, exemplary phenolic compounds of the invention can include, but are not limited to, flavonoids and their derivatives (e.g., anthocyanins, quercetin), flavolignans, phenolic rhizomes, flavan-3-ols including (+)-catechin and (−)-epicatechin, other tannins and derivatives thereof (such as tannic acid, pentagalloylglucose, nobotanin, epigallocatechin gallate, and gallotannins), ellagic acid, procyanidins, and the like.

Phenolic compounds of the invention include synthetic and natural phenolic compounds. For example, natural phenolic compounds can include those found in extracts from natural plant-based sources such as extracts of olive oil (e.g., hydroxytyrosol (3,4-dihydroxyphenylethanol) and oleuropein, extracts of cocoa bean that can contain epicatechin and analogous compounds, extracts of *Camellia* including *C. senensis* (green tea) and *C. assaimic*, extracts of licorice, sea whip, aloe vera, chamomile, and the like.

In one preferred embodiment, the phenolic compounds of the invention can be tannins and derivatives thereof. Tannins can be found in many plant species. For example, the tea plant (*Camellia sinensis*) has a naturally high tannin content. Green tea leaves are a major plant source of tannins, as they not only contain the tannic and gallic acid groups, but also prodelphinidin, a proanthocyanidin. Tannins are also found in wine, particularly red wine as well as in grape skins and seeds. Pomegranates also contain a diverse array of tannins, particularly hydrolysable tannins.

Figure 2:
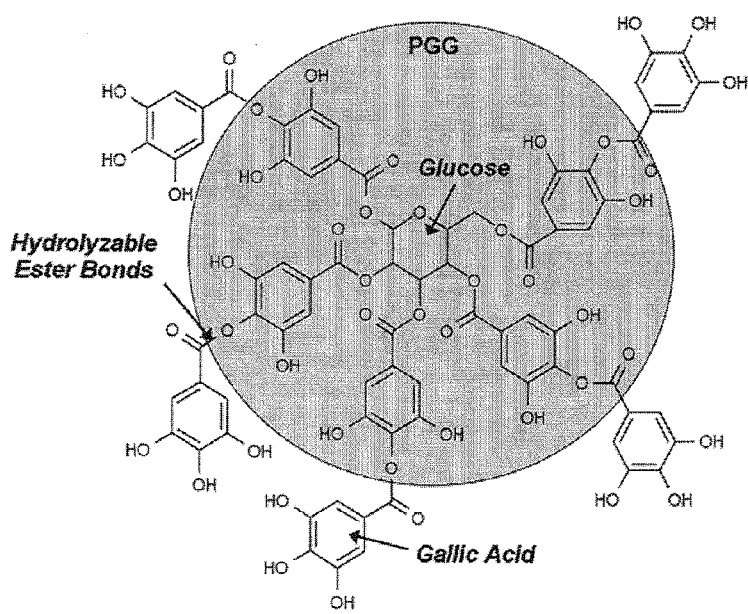
FIG. 2 illustrates the chemical structure of tannic acid, with pentagalloylglucose highlighted by the circle.

Tannic acid, the structure of which is illustrated in FIG. 2, is a common naturally derived tannin. Tannic acid, as a cross-linking agent, is similar in many properties to that of many fixatives often used in the preparation and formation of xenograft or allograft tissue implants, for instance glutaraldehyde fixatives. Moreover, tannic acid can interact with other connective tissue components as well as elastin, and thus can stabilize additional components of the targeted connective tissue in the disclosed processes, in addition to the elastin component. For instance, tannic acid is capable of cross-linking glycosaminoglycan polysaccharides as well as other connective tissue components.

In one embodiment, the present invention is directed to utilization of the disclosed agents for stabilization of connective tissue in vivo. Accordingly, in such embodiments, biocompatibility and cytotoxicity of the agents can be of importance in preparation of therapeutics including the disclosed compounds. At one time, tannic acid-containing preparations were suspected of causing hepatoxicity. This toxicity has since been primarily attributed to poor purity of the preparations and the inclusion of toxic gallic acid residues in the compositions. Accordingly, in one embodiment, the present invention is directed to compositions including high purity tannic acid, with little or no free gallic acid residue included in the compositions. For example, in one embodiment, the compositions of the present invention can include less than about 5% free gallic acid residue in the preparation. In one embodiment, the compositions of the present invention can include between about 1% and about 5% free gallic acid residue in the composition.

In one preferred embodiment of the present invention, compositions are disclosed comprising an effective amount of pentagalloylglucose (PGG). PGG, which is the portion of a tannic acid molecule enclosed in the circle in FIG. 2, includes the hydrophobic core of tannic acid as well as multiple phenolic hydroxy groups, but does not posses the outer gallic acid residues and the hydrolyzable ester bonds associated with tannic acid. Thus, the possibility of release of free gallic acid residues over the course of a long-term application process can be prevented in one embodiment of the invention through utilization of a compound having no gallic acid residues, such as PGG, as the selected agent.

In general, the phenolic compounds described herein can be provided as a biocompatible composition. For instance, compositions disclosed herein can include one or more phenolic compounds in a concentration that can vary over a wide range, with a preferred concentration generally depending on the particular application, the delivery site targeted by the phenolic compound and the mode that will be used in the delivery process. For example, in one embodiment, a composition of the invention can include one or more phenolic compounds at a concentration from about 0.0001% to about 10%. (Unless otherwise noted, all concentrations reported herein are weight/volume percentages.) It should be noted, however, that while these exemplary concentrations are effective in certain embodiments, the invention encompasses compositions comprising a wider range of phenolic compound concentrations. For example, actual concentrations used may be influenced by the organ targeted by the procedure, size of the targeted area, desired incubation time, and preferred pH, in addition to delivery mode, as mentioned above. In one embodiment of the present invention, the disclosed compositions can include concentrations of a phenolic compound ranging from about 0.1% to about 1%.

In one embodiment, the phenolic compounds can be provided in pharmaceutically acceptable formulations using formulation methods known to those of ordinary skill in the art. These formulations can generally be administered by standard routes. For example, the formulations may be administered in one embodiment directly to connective tissue, for instance through exposure of the connective tissue and direct application thereto, or via direct injection of the formulation to the targeted connective tissue. In other embodiments, however, the formulations may be administered indirectly to the targeted tissue.

The formulations can be delivered intravenously in a systemic delivery protocol. For example, osmotic mini-pumps may be used to provide controlled delivery of high concentrations of the treatment agents through cannulae to the site of interest, such as directly into a targeted blood vessel. In situ polymerizable hydrogels, as are generally known to those of skill in the art, and discussed further below, are another example of a delivery vehicle that can be utilized in a delivery protocol, for instance in an intravenous delivery directly to targeted cannulae. Once delivered to the targeted blood vessel by any suitable method as is accepted in the art, the phenolic compound can penetrate the vessel wall and stabilize the connective tissue of the vessel. For instance, when delivered to the connective tissue from the lumen of a blood vessel, the phenolic compounds disclosed herein penetrate the endothelium of the vessel wall to contact the elastin of the connective tissue and stabilize the structure architecture.

Compositions of the present invention can include additional agents, in addition to the phenolic compounds. Such agents can be active agents, providing direct benefit to the tissue in addition to the stabilization provided by the phenolic compound, or may be supporting agents, improving delivery, compatibility, or reactivity of other agents in the composition. For example, in one embodiment, the compositions can include glutaraldehyde. Glutaraldehyde, when targeted to connective tissue, can form covalent cross-links between free amines in proteins in order to further stabilize the tissue. If desired, the composition can incorporate a gallic acid scavenger, for example ascorbic acid or glutathione, so as to prevent the release of free gallic acid residues.

The phenolic compounds can be combined with any of a number of possible lipid-lowering medications so as to prevent the development of calcified lipid deposits or arteriosclerosis plaques that can often be found in conjunction with aneurysm formation.

A phenolic composition of the invention can include one or more buffers as are generally known in the art. For example, a composition including one or more phenolic compounds and having a pH from about 4.0 to about 9.0 may be formulated with inclusion of a biocompatible buffer such as distilled water, saline, phosphate buffers, borate buffers, HEPES, PIPES, and MOPSO. In one embodiment, a composition of the invention may be formulated to have a pH of between about 5.5 and about 7.4.

Compositions for parenteral delivery, e.g., via injection, can include pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. In addition, the composition can contain minor amounts of auxiliary substances such as wetting or emulsifying agents, pH buffering agents and the like that can enhance the effectiveness of the phenolic compound. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents.

Prevention of the action of microorganisms may be ensured by the inclusion of various antibacterial and antifungal agents such as paraben, chlorobutanol, phenol, sorbic acid and the like. It may also be desirable to include isotonic agents such as sugars, sodium chloride and the like.

In one embodiment, the compositions can include pharmaceutically acceptable salts of the components therein, e.g., those that may be derived from inorganic or organic acids. Pharmaceutically acceptable salts are well known in the art. For example, S. M. Berge, et al. describes pharmaceutically acceptable salts in detail in *J. Pharmaceutical Sciences* (1977) 66:1 et seq., which is incorporated herein by reference. Pharmaceutically acceptable salts include the acid addition salts that are formed with inorganic acids such as, for example, hydrochloric or phosphoric acids, or such organic acids as acetic, tartaric, mandelic and the like. Salts formed with free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. The salts may be prepared in situ during the final isolation and purification of the compounds of the invention or separately via reaction of a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptonoate, hexanoate, fumarate, hydrochloride, hydrobromide, hydroiodide, 2-hydroxymethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl, and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

In one embodiment the method can include use of timed release or sustained release delivery systems as are generally known in the art. Such systems can be desirable, for instance, in situations where long term delivery of the agents to a particular organ or vascular location is desired. According to this particular embodiment, a sustained-release matrix can include a matrix made of materials, usually polymers, which are degradable by enzymatic or acid/base hydrolysis or by dissolution. Once located at or near the target tissue, e.g., inserted into the body, for instance in the form of a patch or a stent such as those further described below, such a matrix can be acted upon by enzymes and body fluids. The sustained-release matrix can be chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Possible biodegradable polymers and their use are described, for example, in detail in Brem et al. (1991, *J. Neurosurg.* 74:441-6), which is hereby incorporated by reference in its entirety.

When an effective amount of the agents of the present invention are administered by intravenous or subcutaneous injection, the compositions can generally be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection can contain, in addition to the phenolic compound of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The treatment composition of the present invention may also contain stabilizers, preservatives, antioxidants, or other additives known to those of skill in the art.

The dosage of the disclosed treatment agents of the present invention can depend on the disease state or particular condition being treated and other clinical factors such as weight and condition of the human or animal and the route of administration of the compound. The disclosed treatment agents can be administered between several times per day to a single treatment protocol. Optionally, treatment agents could be delivered according to the disclosed process either acutely, during a one-time intervention, or chronically, for instance using multiple administrations or optionally a single administration of a timed or sustained releases system. It is to be understood that the present invention has application for both human and veterinary use. The methods of the present invention contemplate single as well as multiple administrations, given either simultaneously or over an extended period of time. In addition, the disclosed treatment agents can be administered in conjunction with other forms of therapy, e.g., surgical endovascular stent graft repair or replacement of an excessively damaged area of vasculature.

Figure 3:
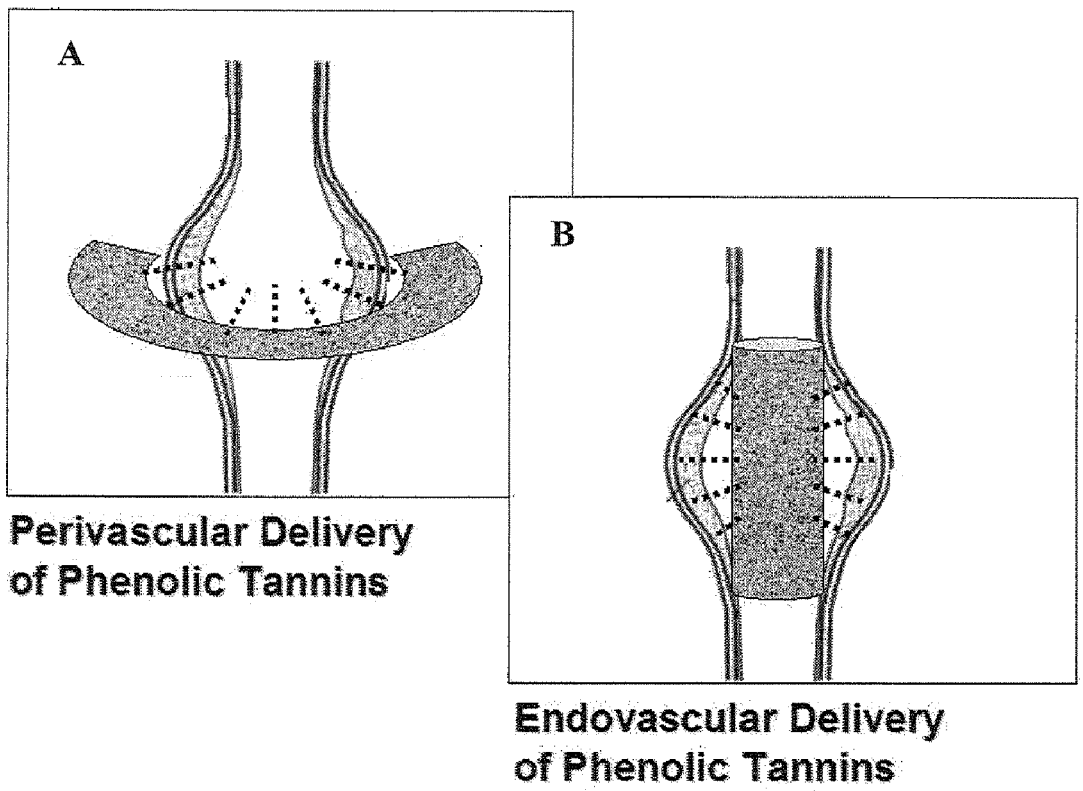
FIG. 3 schematically illustrates exemplary delivery methods for phenolic compounds according to certain embodiments of the present invention including perivascular delivery (FIG. 3A) and endovascular delivery (FIG. 3B)

In one embodiment, a composition including one or more phenolic compounds can be targeted to a specific site, such as to a diagnosed aneurysm in vivo, using a minimally invasive procedure to provide long-term delivery of the treatment agent locally from a biocompatible implantable device. For example, FIG. 3 schematically illustrates possible perivascular (FIG. 3A) and endovascular (FIG. 3B) routes of delivery, either of which could be utilized for local targeted delivery of the disclosed treatment agents, for instance to a diagnosed aneurysm.

Perivascular delivery technologies suitable for use in the present invention are generally known to those of skill in the art, and thus need not be explained at length herein. For instance, exemplary known perivascular drug delivery technologies include those described by Chen, et al. (U.S. patent Application Publication No. 2005/0079202) and Nathan (U.S. Patent Application Publication No. 2003/0228364), both of which are incorporated herein by reference. These exemplary perivascular delivery systems include a polymeric delivery vehicle that can be injected or directly placed, for instance via surgery, at a particular location so as to provide controlled release of the phenolic compound encapsulated or otherwise loaded therein over a period of time.

A phenolic compound of the invention can be loaded in a drug delivery vehicle via encapsulation, coating, infusion, or any other loading mechanism as is known in the art.

Prolonged absorption of an injectable pharmaceutical form may be brought about by the inclusion of agents, such as aluminum monostearate and gelatin, which can delay absorption. For example, injectable depot forms can be made by forming microencapsule matrices including the phenolic compound loaded in the matrix formed of biodegradable polymers such as polylactide-polyglycolide, poly(orthoesters) and poly(anhydrides). Depending upon the ratio of therapeutic agent to polymer and the nature of the particular polymer employed, the rate of drug release can be controlled. Depot injectable formulations can also be prepared by entrapping the therapeutic agents in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use.

Many endovascular drug delivery methods are likewise known in the art. For example, DiCarlo, et al. (U.S. Pat. No. 6,929,626, incorporated herein by reference) describe an intraluminally placeable tubular device that can be located within the lumen of a blood vessel and coated or otherwise loaded with a drug, e.g., the phenolic compounds described herein. The tubular member includes yarns interconnected in a pattern defining opposed interior and exterior textile surfaces. At least one of the textile surfaces is the body fluid-contacting luminal surface or the body lumen-contacting exterior surface.

Wu, et al. (U.S. Pat. No. 6,979,347, incorporated herein by reference) describe an apparatus and associated method for delivering a therapeutic substance such as the phenolic compounds of the present invention, to a vascular lumen. Specifically, an implantable prosthesis, such as a stent, can be utilized that has grooves or trenches formed thereon. The grooves are formed on specific regions of the stent struts to increase the flexibility of the stent. The grooves also provide a location for carrying the phenolic compound for delivery from the device following implantation. For example, the phenolic compound, or a composition thereof, can be deposited directly in to the grooves using conventional spray or modified dip techniques.

In another embodiment, the disclosed agents can be targeted to connective tissue by use of a hydrogel delivery vehicle. Hydrogels are herein defined to include polymeric matrices that can be highly hydrated while maintaining structural stability. Suitable hydrogel matrices can include un-crosslinked and crosslinked hydrogels. In addition, crosslinked hydrogel delivery vehicles of the invention can optionally include hydrolyzable portions, such that the matrix can be degradable when utilized in an aqueous environment, e.g., in vivo. For example, the delivery vehicle can include a cross-linked hydrogel including a hydrolyzable cross-linking agent, such as polylactic acid, and can be degradable in vivo.

Hydrogel delivery vehicles of the present invention can include natural polymers such as glycosaminoglycans, polysaccharides, proteins, and the like, as well as synthetic polymers, as are generally known in the art. A non-limiting list of hydrophilic polymeric materials that can be utilized in forming hydrogels of the present invention can include dextran, hyaluronic acid, chitin, heparin, collagen, elastin, keratin, albumin, polymers and copolymers of lactic acid, glycolic acid, carboxymethyl cellulose, polyacrylates, polymethacrylates, epoxides, silicones, polyols such as polypropylene glycol, polyvinyl alcohol and polyethylene glycol and their derivatives, alginates such as sodium alginate or crosslinked alginate gum, polycaprolactone, polyanhydride, pectin, gelatin, crosslinked proteins peptides and polysaccharides, and the like.

Hydrogels of the present invention can be formed according to any method as is generally known in the art. For instance, the hydrogel can self-assemble upon contact of the various components or upon contact in conjunction with the presence of particular environmental conditions (such as temperature or pH). Alternatively, assembly can be induced according to any known method following combination of the components. For example, step-wise or chain polymerization of multifunctional monomers, oligomers, or macromers can be induced via photopolymerization, temperature dependent polymerization, and/or chemically activated polymerization. Optionally, the hydrogel can be polymerized in the presence of an initiator. For example, in one embodiment, the hydrogel can be photopolymerized in the presence of a suitable initiator such as Irgacure® or Darocur® photoinitiators available from Ciba Specialty Chemicals. In another embodiment, a cationic initiator can be present. For example, a polyvalent elemental cation such as $Ca^{2+}$, $Mg^{2+}$, $Al^{3+}$, $La^{3+}$, or $Mn^{2+}$ can be used. In another embodiment, a polycationic polypeptide such as polylysine or polyarginine can be utilized as an initiator.

The components of the hydrogel delivery vehicle can also be designed so as to provide a self-assembling delivery vehicle. For example, a hydrogel precursor can be administered to a subject, and the hydrogel matrix can self-assemble at physiological conditions following administration of the precursor. For instance, the hydrogel precursor can include self-assembling biopolymers such as collagens, laminins, pro-elastin peptides, and the like. Optionally, a self-assembling hydrogel precursor can include synthetic polymers that can array themselves according to domains, as is generally known in the art. For example, hydrophilic, relatively charge-neutral synthetic polypeptides such as polyglycine or polylysine can be modified to function in this capacity. Polypeptides can be crosslinked by using carboxy-activating crosslinking agents such as water-soluble carbodiimides. Such cross-linking agents can be used to attach self-assembling proteins or other self-assembling macromolecules to the polypeptides. One example of this approach includes formation of a carbodiimide linkage of collagen or laminin with polylysine. Other hydroxylated entities can be linked in a similar manner. For example, in one embodiment, polyvinyl alcohol can be linked with polypeptides using an epoxy-activation approach or crosslinked via polymerizable methacrylate groups along its side chains, as is known in the art.

In another embodiment, a self-assembling hydrogel can be generated by use of precursors that have been derivatized to contain favorably reactive groups. For example, a hydrogel of this type could be assembled using a first precursor derivatized with a particular reactive moiety and a second precursor derivatized with or comprising a second moiety that can preferentially react with the first moiety on the first precursor. Likewise, other such hydrogels could be generated using such reactive pairs wherein the two moieties that react to form the bond are each conjugated to the same or a different type of polymer. For example, the pairs can be antibody-antigen pairs or avidin-biotin (e.g. streptavidin-biotin).

In other embodiments a hydrogel delivery vehicle need not be a self-assembling matrix. For example, in other embodiments a hydrogel matrix for use in vivo can be administered to a patient according to a suitable administration method (e.g., percutaneously) following assembly of the hydrogel. In other embodiments of the invention, the disclosed systems can be utilized in ex vivo applications, for example in tissue engineering applications, and as such, the carrier matrix of the invention need not be a self-assembling matrix.

The delivery vehicles of the present invention can include a combination of one or more delivery vehicles. For instance, a hydrogel delivery vehicle can be combined with a patch, a stent, a perforated balloon, a vascular graft, or any other suitable device, for delivery of the disclosed agents to connective tissue.

Delivery vehicles of the invention can also include vascular grafts. For example, an allograft, xenograft or autologous graft can be associated with a phenolic compound as herein described prior to implantation. For example, the vascular graft can be coated with a phenolic compound or a composition including a phenolic compound as herein described. In another embodiment, a vascular graft can be associated with a hydrogel delivery vehicle or a non-hydrogel polymeric delivery vehicle such as those described above that has in turn been loaded with the phenolic compound. During implantation, the vascular graft can be located in association with the targeted connective tissue, and thus serve to deliver the phenolic compound to the tissue.

Reference now will be made to exemplary embodiments of the invention set forth below. Each example is provided by way of explanation of the invention, not as a limitation of the invention. In fact, it will be apparent to those skilled in the art that various modifications and variations may be made of this invention without departing from the scope or spirit of the invention.

EXAMPLES

Materials utilized in all examples were obtained as follows: Tannic acid, glutaraldehyde (50% solution), and other high purity chemicals were obtained from Sigma-Aldrich (St. Louis, Mo.). Diethyl ether was obtained from Acros Organics (Morris Plains, N.J.). Ethyl acetate was acquired from EM Science (Gibbstown, N.J.). High purity porcine pancreatic elastase (135 U/mg) was purchased from Elastin Products Company, Inc. (Owensville, Mo.). Dulbecco's modified eagle media (DMEM) and fetal bovine serum (FBS) were obtained from Cellgro (Herndon, Va.). Penicillin-streptomycin for cell culture was obtained from Invitrogen (Carlsban, Calif.). CellTiter 96® $AQ_{ueous}$ One Solution Reagent (for MTS) was from Promega (Madison, Wis.). The LIVE/DEAD® Viability/Cytotoxicity Kit was obtained from Molecular Probes (Eugene, Oreg.).

Ascending porcine aorta (supravalvular segments, approximately 3 cm in length) were collected fresh from USDA-approved slaughterhouses and transported on ice. Aorta was cleaned of fat and extraneous tissue, rinsed exhaustively in cold physiological saline, and cut into various shapes appropriate for each example.

Example 1

Fresh porcine aorta was cut into approximately 4 mm×4 mm squares and treated with 0.3% tannic acid (TA) (1.76 mM) in 50 mM HEPES ($Na_2HPO_4$) buffered saline at pH 5.5 for 4 days at room temperature. A control sample was treated in mM Hepes buffered saline at pH5.5. Samples were then rinsed three times (1 hour each) in 100 mL ddH$_2$O at room temperature and lyophilized to record dry weight. Samples (about 15-25 mg dry weight), both control and TA treated, were incubated with 1.0 mL pure elastase (20 units/ml, in 100 mM Tris, 1 mM CaCl$_2$, 0.02% NaN$_3$, pH 7.8 buffer) at 37° C. for 48 hours with orbital shaking at 650 rpm. Samples were then centrifuged (10000 rpm, 10 min. 4° C.) and supernatants retained to assess enzyme activity. Tissue samples were again rinsed three times (1 hour each) in 100 mL ddH$_2$O at room temperature and lyophilized to record dry weight after elastase, and the percent of digested tissue was calculated. Elastin degradation was assessed by measuring mass loss (dry weight before and after elastase contact) and by preparation of histological slides stained with an elastin-specific stain (Voerhoff van Gieson stain).

Figure 4:
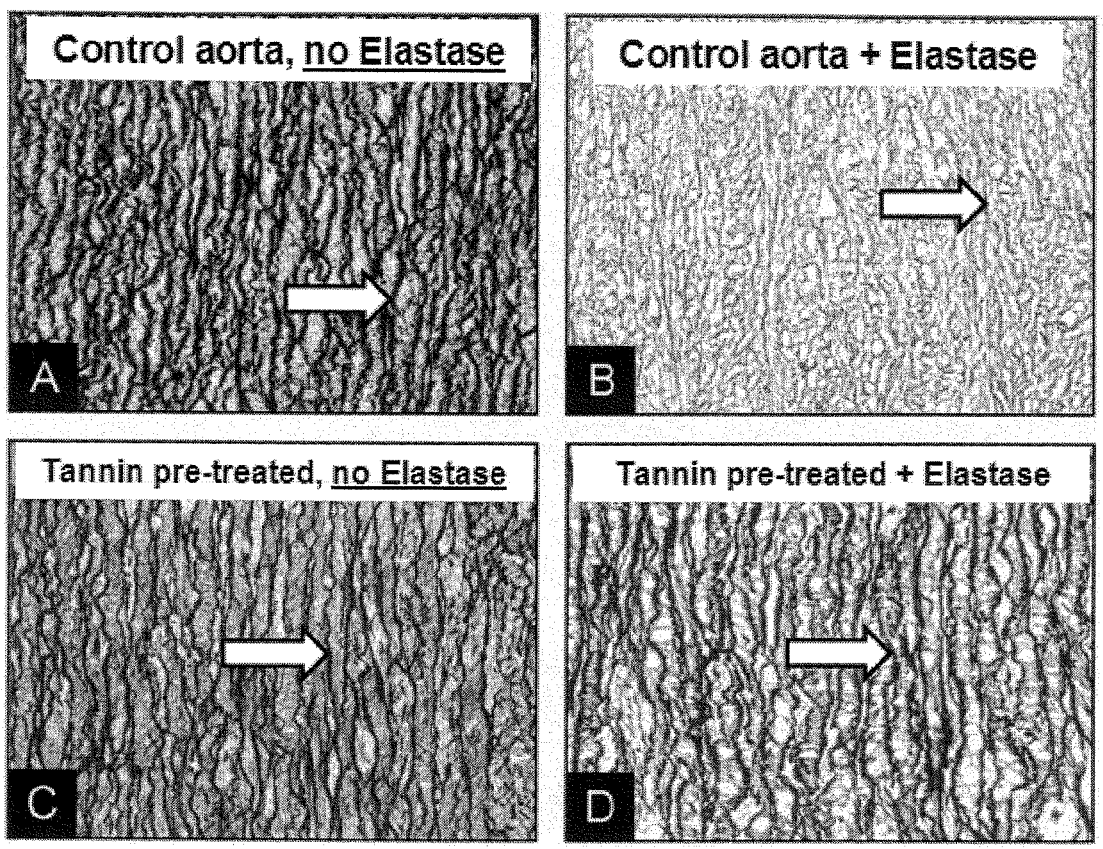
FIGS. 4A-4D show stained aortic tissue sections described in the example section illustrating stabilization of elastin of the connective tissue in the presence of elastase.

Upon assessment, the control samples were found to have lost almost 80% of the mass (average, 79.74%, n=6), while the TA pre-treated samples lost only 4-5% of the mass (average 4.33%, n=6). Histology showed that elastin fibers were completely digested by elastase in the control samples, while in TA pre-treated samples, elastin fibers were fully preserved, as can be seen in FIGS. 4A-4D, which illustrate the results of the histology study. FIGS. 4A-4D show aortic tissue sections stained with Voerhoff van Gieson stain, which reveals elastin fibers as dark ribbons. In particular, FIGS. 4A and 4B show the fresh control aorta before and after the procedure, respectively, and FIGS. 4C and 4D illustrate the TA pre-treated samples before and after the procedure, respectively. As can be seen, elastin was completely digested by the elastase in the control aorta (FIG. 4B), as compared to full preservation of the elastin the TA pre-treated aorta (FIG. 4D). The arrows in the Figures point to locales including the preserved elastin (FIGS. 4A, 4C, and 4D) and the digested elastin (FIG. 4B).

Example 2

Fresh porcine aorta was cut across the diameter into continuous rings approximately 1 cm in height as illustrated in FIG. 5A and treated with glutaraldehyde (Glut treatment). For this treatment, aortic ring samples were first fixed with 0.6% glutaraldehyde in 50 mM Hepes buffered saline, pH 7.4, overnight at room temperatures, followed by 0.2% glutaraldehyde in the same buffer for 7 days at room temperatures.

A portion of the Glut-treated rings were then treated with 0.3% pentagalloylglucose (PGG). PGG was first prepared from TA as outlined by Hagerman, et al. (Hagerman A. E., Zhao Y., and Johanson J., "Methods for determination of condensed and hydrolyzable tannins," Shahadi, F., Ed., *Antinutrients and Phytochemicals in Foods*, Washington, D.C., American Chemical Society, p. 209-222 (1997)). Specifically, TA was methanolyzed using a solution of methanol and acetate buffer. After methanolysis, the methanol was removed by rotary evaporation and replaced with ddH$_2$O. A series of separate extractions involving diethyl ether and ethyl acetate, along with rinses of dilute methanol and ddH$_2$O was performed to purify the PGG. The resulting precipitate was centrifuged and lyophilized to form a solid. The purity of PGG was confirmed by MALDI mass spectroscopy and NMR. A portion of the Glut-treated tissue was then treated with PGG in the same buffer for 4 days (Glut/PGG treatment, marked as PGG on FIG. 5).

Figure 5:
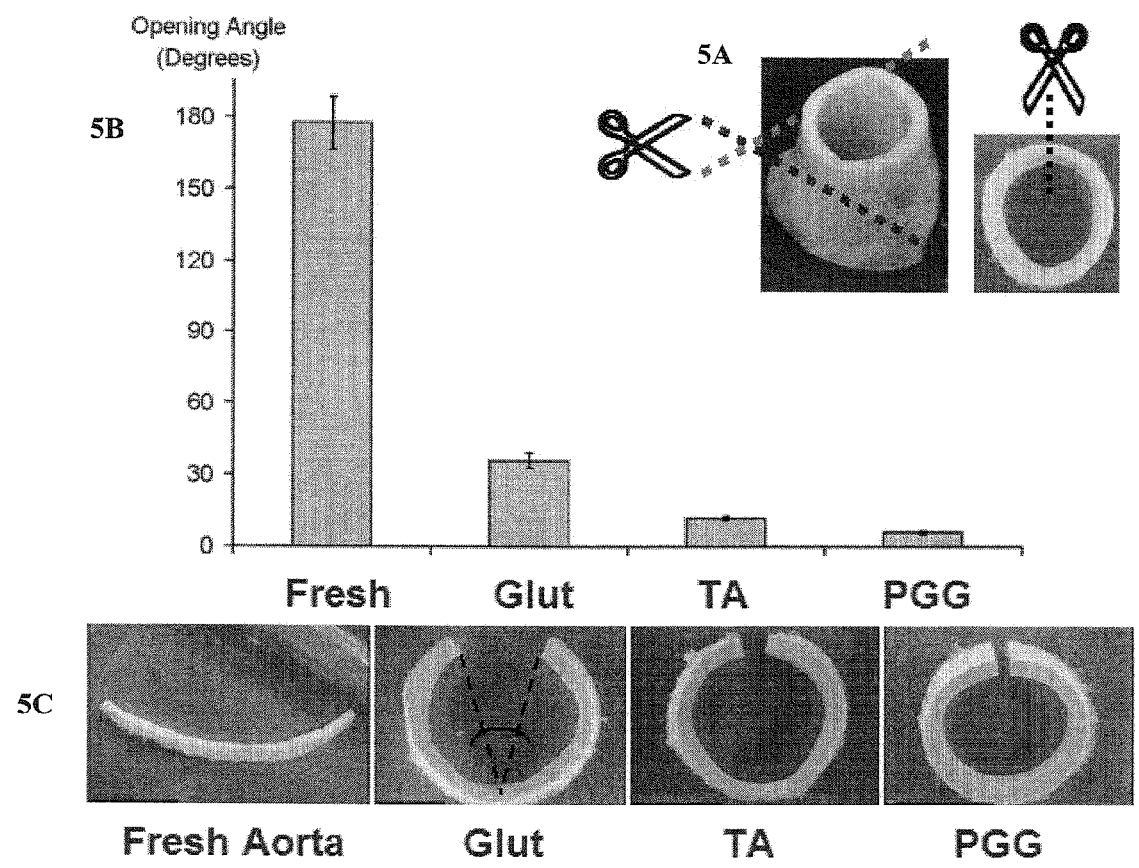
FIG. 5A illustrates the procedures used for examination of the opening angle of a section of porcine aorta and as described in the example section.
FIG. 5B graphically illustrates the results of the determination of the opening angle of the sections of porcine aorta.
FIG. 5C includes photographs of the porcine aorta sections showing recoil evaluation of treated and control tissue samples.

Another Glut-treated sample was treated with TA according to the same procedure (Glut/TA treatment, marked as TA on FIG. 5), and a control sample was treated in only the buffer (marked as Fresh on FIG. 5).

Samples were then tested for ability to recoil using opening angle measurements. Specifically, each ring was placed in a dish of water (enough to completely cover the tissue) with the cross section of the aorta facing upward, allowing free movement of the sample. The rings were then cut once in the radial direction, allowed to relax and open for 15 minutes, and then digitally photographed. These digital photographs were imported into Adobe® Photoshop® 7.0 and lines were created for each sample between the tip of the cut edges and the midpoint of the luminal wall opposite the location of the radial cut, as shown in the Glut sample photograph in FIG. 5C. Using these lines, the opening angles of the aortic rings were calculated. Results are illustrated in FIG. 5B and Table 1, below, including standard error of the mean (SEM) values.

To evaluate mechanical properties, aorta was cut to form dumbbell shapes approximately 40 mm in length, approximately 10 mm wide at each end, and approximately 5 mm wide at the center, with the long axis of the dumbbell shape being parallel to the circumferential direction of the aorta. Tensile properties of the samples were tested using standard stress/strain analysis on a Synergie 100 testing apparatus (MTS Systems Corporation, Eden Prairie, Minn.) operated at a constant uniaxial velocity of 0.2 mm/sec using a 10-Newton load cell to determine elastic modulus of the samples. Elastic modulus was calculated as the slope of the stress-strain curve between 0 and 5% strain. Results are shown below in Table 1.

TABLE 1

| Pre-treatment | Mean opening angle (degrees) | SEM (n = 5) | Mean Elastic Modulus (kPa) | SEM (n = 4) |
|---|---|---|---|---|
| Control | 177.50 | 11.0 | 0.16 | 0.01 |
| Glut | 35.9 | 3.3 | 1.28 | 0.04 |
| Glut/TA | 11.8 | 0.7 | 4.85 | 0.30 |
| Glut/PGG | 5.9 | 0.7 | 4.61 | 0.40 |

As can be seen, Glut/TA and Glut/PGG treated rings exhibited much smaller opening angles, indicating that tannic acid interacted with the elastin component and did not fully allow recoil to occur. Similarly, the calculated elastic modulus was increased following treatment with tannic acid and PGG. These results suggest that the tannins bind strongly to the elastic components of the tissue and in doing so stiffen and strengthen the tissue.

Example 3

Fresh porcine aorta was treated with Glut, Glut/TA, or Glut/PGG, as described above. After thorough rinsing (3×, 1 hr. each, 100 mL ddH$_2$O), samples were orbitally shaken at 120 rpm 37° C. for 14 days in a PBS/azide buffer, pH7.4, for extraction of soluble, cytotoxic compounds (50 mL per 6 tissues samples, each 4 mm×4 mm).

Rat skin fibroblasts were seeded onto 24-well plates (50,000 cells/well) in 1 mL DMEM supplemented with 10% FBS and 1% penicillin-streptomycin. Cells were maintained in a humidified incubator at 37° C. with 10% CO$_2$. After 24 hours, the media was removed and replaced with one of the PBS/azide solutions diluted 10-fold in fresh media. As control, a sample was held in buffer alone (negative control) and also in a 70% ethanol solution (positive control). Effectively, 100 µL of the 'test solution' was added to 900 µL of media for each well (except in the case of ethanol, in which no media was added). The cells were incubated with these solutions for 2 hours and then rinsed with 1 mL PBS. Viability of the cells was then assessed using a qualitative LIVE/DEAD® staining fluorescent stain. In addition, a quantitative measurement, MTS, was used to measure the activity of cell enzymes.

Specifically, the reagent was diluted 5-fold in media, then applied to the cells for 90 minutes. A portion of the resulting solutions (100 μper well) was transferred to a 96-well plate and read at an absorbance of 490 nm. Samples were blanked to a well containing media and MTS reagent with no cells.

Figure 6:
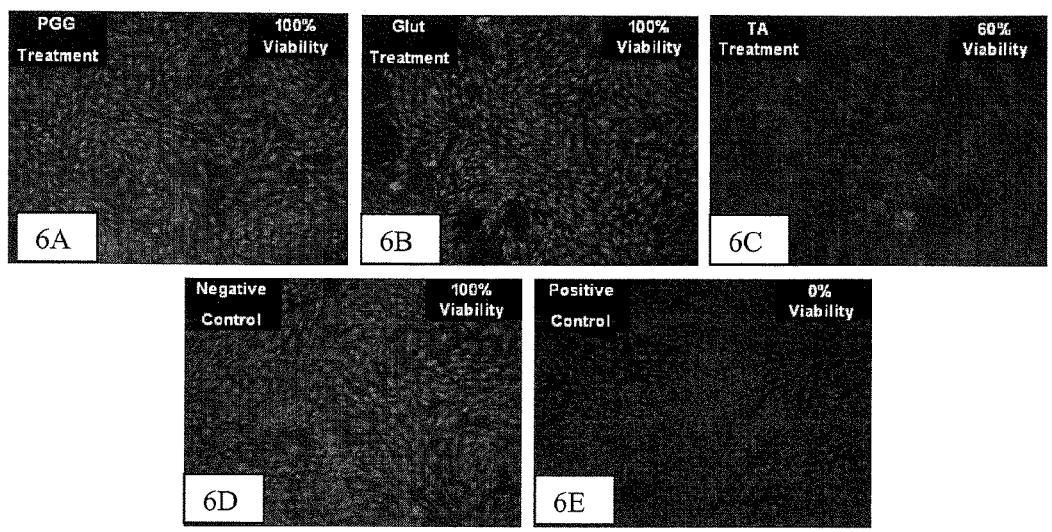
FIGS. 6A-6E are digital photographs showing results for the live/dead assay of treated tissue samples as described in the example section.

Micrographs of cells introduced to LIVE/DEAD® were taken 45 minutes after exposure. Results are shown in FIGS. 6A-6E, in which living cells appear as light spots on the dark background, and dead cells appear as darker gray spots. As can be seen with reference to the Figures, cells exposed to extracts from Glut (FIG. 6B) and Glut/PGG-treated (FIG. 6A) tissue remained viable after 2 hours of exposure. In addition, it appeared that the small concentration of azide had little or no effect on cytotoxicity in this time frame, as suggested by the presence of live cells in the PBS/azide group (FIG. 6D). However, cells that were introduced to extracts from Glut/TA-treated aorta experienced a notable amount of cell death (about 40%, FIG. 6C). As expected, the EtOH negative control left essentially no viable cells (FIG. 6E).

Quantitative results from the MTS assay are given below in Table 2. These results suggest that phenolic tannins are generally not cytotoxic, but PGG appears to be less cytotoxic than TA.

TABLE 2

| Pre-treatment | Viability (live/dead assay) | Viability (MTS assay) | SEM (n = 3) |
|---|---|---|---|
| Glut | 100% | 1.04 | |
| Glut/PGG | 100% | 0.94 | 0.03 |
| Glut/TA | 60% | 0.53 | 0.06 |
| EtOH | 0% | 0.03 | 0.02 |
| PBS/azide | 100% | 1.04 | 0.00 |

Example 4

Ascending porcine aorta was collected fresh at a slaughterhouse and transported to the laboratory on ice. After cleaning fat and adherent tissues, aorta was cut into 2×4 mm strips and thoroughly rinsed in cold saline. Aortic elastin was purified by a sequence of extractions. Specifically, aortic strips were suspended in 100 mM sodium hydroxide (60 strips in 100 mL) and incubated for 14 hours at 37° C. with collagenase (0.5 units/mg wet tissue) in 50 mM Tris buffer, 10 mM calcium chloride, pH 8.0. The collagenase preparation was pre-adsorbed with elastin fibers to remove residual elastolytic activities. The final digestion step completely removed residual collagen, leaving pure aortic elastin.

The pure aortic elastin strips were placed in 2 mL microfuge tubes and suspended in 1.5 mL of an 8 mg % TA solution prepared in a 50 mM disodium hydrogen phosphate, 0.9% sodium chloride buffer, pH 5.5. A second group consisted of pure aortic elastin suspended in a solution containing 8 mg % TA and 16 mg % Glut in the same buffer. As controls, TA solution and the mixture of TA and Glut were incubated without elastin samples. Samples were incubated at room temperature and at defined time intervals (0, 20, 40, 60, 120, 360 minutes and 24 hours), samples were retrieved and analyzed for TA content in solution. Specifically, samples were mixed with a tungstate/phosphomolybdate reagent followed by addition of a saturated sodium carbonate solution and ddH2O. After 10 minutes at room temperature, OD at 760 nm was measured in a microplate spectrophotometer. Standard curves were constructed with TA in the range of 0-8 mg % and with TA (0-8 mg %) in mixtures with Glut (16 mg %). Glut interference with the TA color reaction was minimal (no statistical differences found for all data points). Finally, the elastin strops were rinsed in ddH2O and lyophilized. The amount of TA bound to pure aortic elastin was calculated from the differences between initial TA concentration in solution and concentration of TA in solution after incubation with elastin strops and were expresses as micrograms of TA bound by 1 mg dry elastin. All samples were assayed in triplicate.

Figure 7:
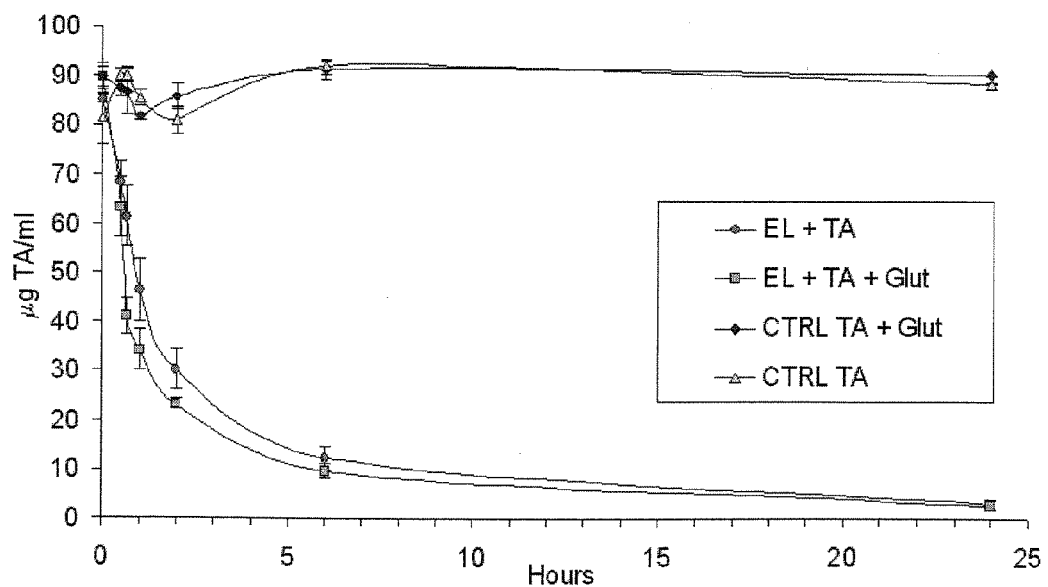
FIG. 7 is a graphic representation showing the kinetics of the binding of tannic acid to pure aortic elastin.

Results are graphically illustrated in FIG. 7. As can be seen with reference to the figure, levels of TA in control solutions incubated without elastin remained constant throughout the study, indicating that the solutions were stable. However, within 1 hour of incubation with elastin, the amount of TA in solution decreased by about 50%, decreasing to 10% after 6 hours, and to less than 3.5% of initial TA at 24 hours, clearly indicating binding of TA to elastin. The kinetics shows a rapid binding within the first 6 hours, leveling off at about 3 mg of TA/mg dry elastin. The binding rate of TA from mixtures of TA and Glut was found to be higher that that of TA alone, suggesting that Glut may facilitate or accelerate binding of TA to elastin.

Example 5

In vivo use of the disclosed agents was examined. The aneurysm model used was based on the perivascular application of a high concentration calcium chloride ($CaCl_2$) solution, a method originally used to induce aneurysms in rabbit carotid arteries (see, Gertz S D, Kurgan A, Eisenberg D. *J Clin Invest* 1988; 81(3):649-656.) and has more recently been used on abdominal aorta of rodents. (See, e.g., Freestone T., et al., *Arterioscler Thromb Vasc Biol* 1995; 15(8):1145-1151. Freestone T., et al., *Arterioscler Thromb Vasc Biol* 1997; 17(1): 10-17. Tambiah J., et al. *Br J Surg* 2001; 88(7):935-940.) This model results in a localized mild insult to the arterial tissue. In most studies, a significant increase in aortic diameter (indicative of aneurysm formation) was observed after 3 to 6 weeks post-injury. For this example, the $CaCl_2$-based chemical injury was performed on rat aorta.

Adult male Sprague-Dawley rats were placed under general anesthesia (2% to 3% isoflurane), allowing for a midline incision along the abdomen in order to expose the infrarenal abdominal aorta. Once exposed, the abdominal aorta was treated with 0.03% PGG solution in saline for 15 minutes using a strip (1.5 cm×0.5 cm) of presoaked 8-ply sterile cotton gauze. The area was then briefly rinsed with saline, allowing induction of chemical injury (0.5 M $CaCl_2$, delivered with gauze for 15 minutes). As controls, rat aortas were treated with physiological saline for 15 minutes, rinsed, and then subjected to calcium chloride. After treating with $CaCl_2$, the gauze was removed and the abdominal cavity was closed with subcutaneous suture, followed by surgical staples. The rats were anesthetized after 28 days, at which point the abdominal aorta was again exposed. Digital photographs (before PGG application at day 0, as well as after 28 days) were used to measure percent increases in diameter after the 28 day period for each rat. Aortic tissue was collected for analysis.

Figure 8:
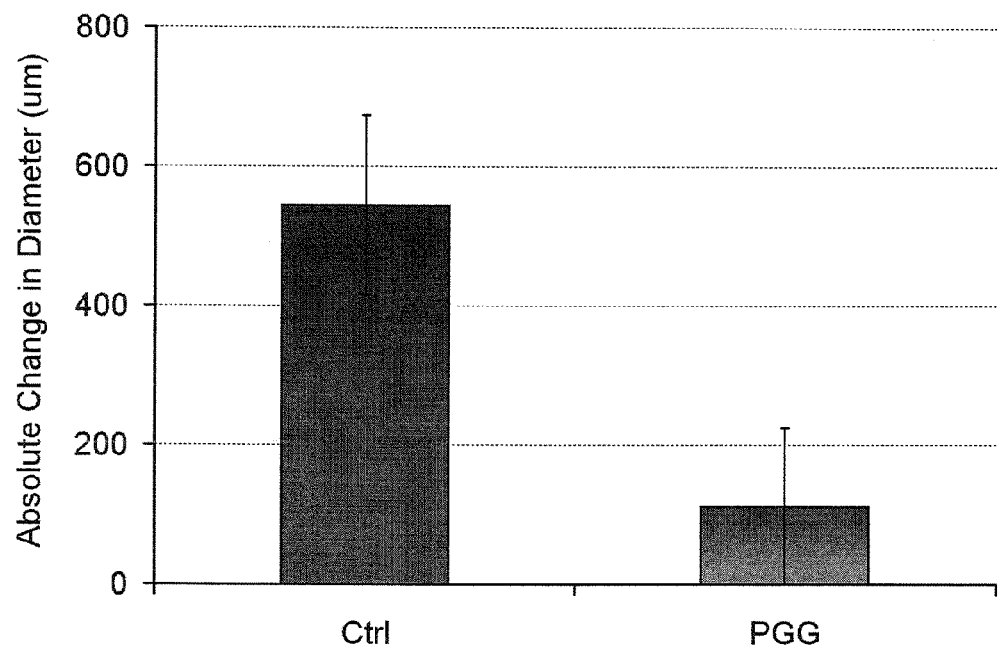
FIG. 8 graphically illustrates the increase in diameter upon injury of rat aortas (no treatment) and illustrates the significant reduction in aneurysm for aortas treated with a phenolic compound as herein described.
Figure 9:
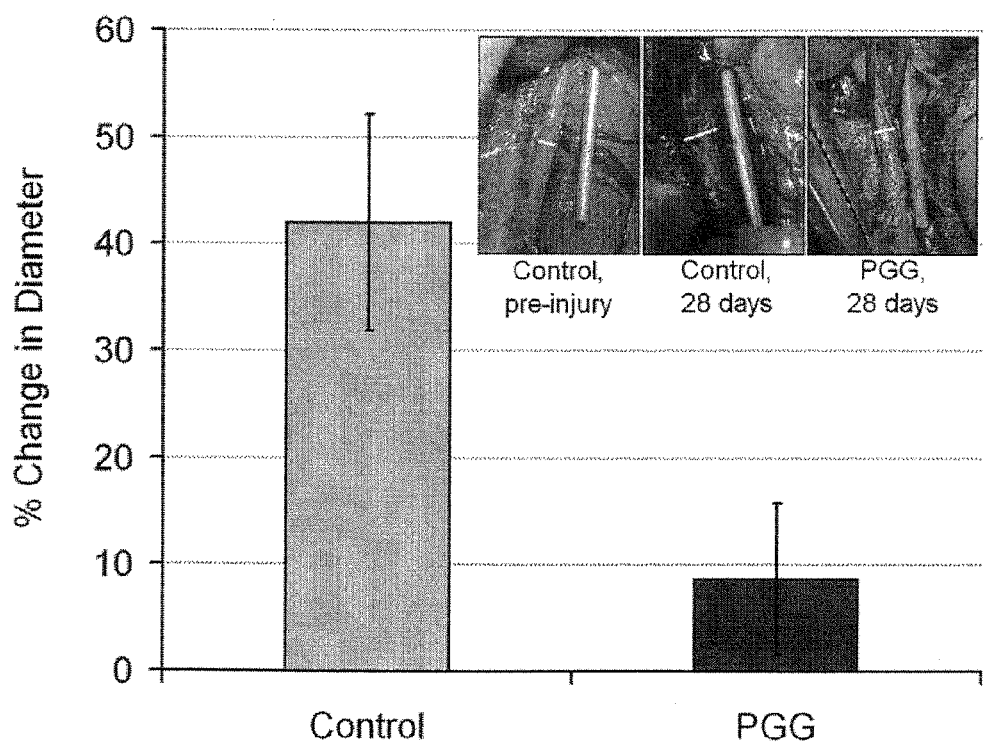
FIG. 9 illustrates the percentage increase in diameter for the control aortas and the treated aortas of FIG. 8.

FIG. 8 graphically illustrates the absolute change in diameter of the aortic segments (n=12 per group). As can be seen, in the control aortas, the increase in diameter of the aortic segments was about 530 μm. In the PGG-treated segments, in contrast, the increase was about 100 μm, and the differences were found to be statistically significant. FIG. 9 inset photographs show an example of a control aorta, pre-injury, a control aorta 28 days post-injury, and a PGG-treated aorta, 28 days post-injury. FIG. 9 graphically shows the results according to the percentage change in diameter of the segments—greater than 40% for the control, and less than 10% for the PGG-treated aortas.

Figure 10A:
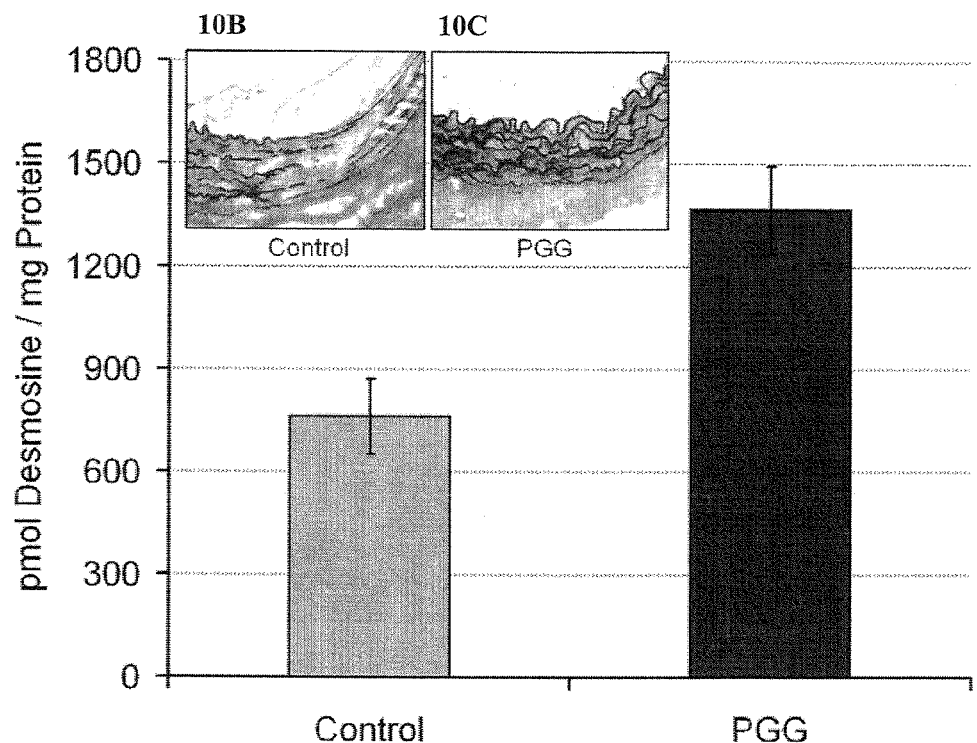
FIG. 10A graphically illustrates the elastin content of the control aortas and the treated aortas of FIG. 8.

Following superficial examination of the aortic segments, the segments were analyzed via desmosine analysis for elastin content. According to the analysis protocol, higher desmosine content implies lower elastin degradation. The results are illustrated in FIG. 10. As can be seen with reference to the Figure, the control included about 750 pmol desmosine/mg protein, while the PTT-treated aortas included about 1350 pmol desmosine/mg protein. FIGS. 10B and 10C illustrate a control aorta and a treated aorta, respectively, following Verhoeff van Giesson staining, which stains elastin black. As can be seen the control aorta has very little elastin, while the treated aorta has retained elastin (shown by the black staining of the elastic fibers in the figures).

Figure 11:
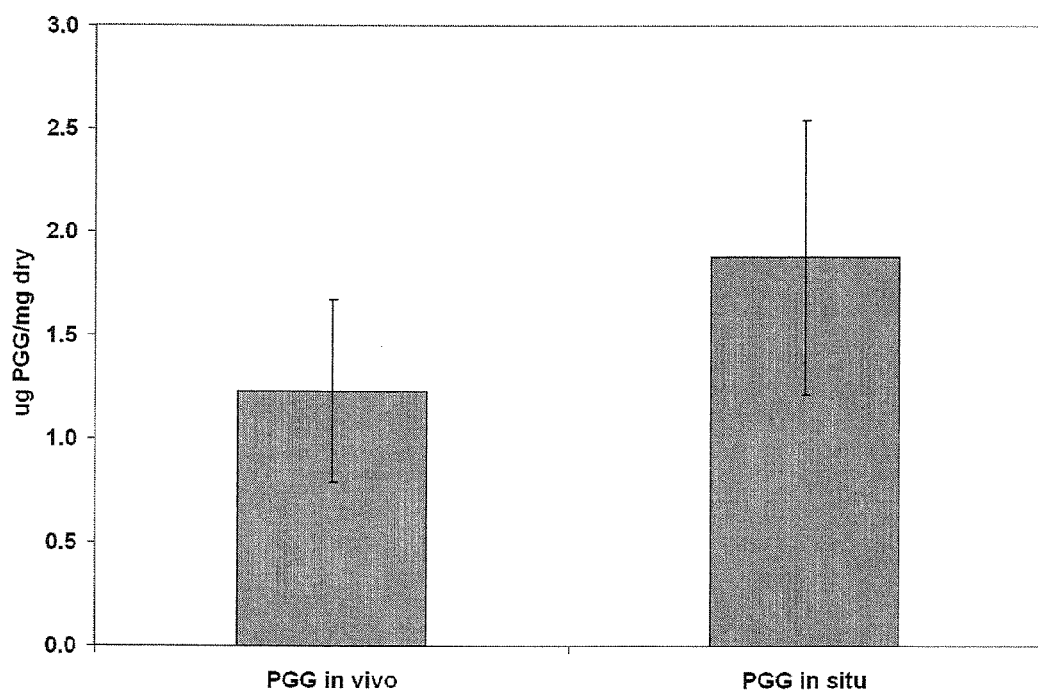
FIG. 11 compares the results following extraction of phenolic compounds from treated tissue immediately following treatment as herein described in situ and 28 days in vivo following treatment.

Vessels were also analyzed to determine the long-term binding of the tannins with the tissue. Tannins were extracted from explanted aorta immediately after treatment (labeled PGG in situ on FIG. 11) and measured levels were compared to those obtained from aorta explanted 28 days following PGG treatment (labeled PGG in vivo on FIG. 11). As can be seen, while the level of tannins found in the tissue dropped somewhat over time, from about 1.8 µg PGG/mg dry tissue to about 1.3 µg PGG/mg dry tissue, a larger percentage of the tannins remained bound to the tissue in vivo for the extended period.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention which is defined in the following claims and all equivalents thereto. Further, it is recognized that many embodiments can be conceived that do not achieve all of the advantages of some embodiments, yet the absence of a particular advantage shall not be construed to necessarily mean that such an embodiment is outside the scope of the present invention.

What is claimed is:

1. A leaky balloon for repair of aneurysm of a blood vessel in a living subject comprising a balloon element and a therapeutic composition contained in the balloon element,
   wherein the balloon element comprises a membrane that allows the therapeutic composition to leak from the balloon element to access the aneurysm,
   wherein the therapeutic composition is substantially free of unbound gallic acid and has a pH between about 4 and about 9, and
   wherein the therapeutic composition comprises a phenolic compound having a plurality of phenolic groups at an effective concentration that crosslinks elastin in the blood vessel in vivo to stabilize the blood vessel.

2. The leaky balloon of claim 1 wherein the phenolic compound is a flavonoid or a flavonoid derivative, a flavolignan or a flavolignan derivative, a phenolic rhizome or a phenolic rhizome derivative, a flavan-3-ol or a flavan-3-ol derivative, a tannin or a tannin derivative, an ellagic acid or an ellagic acid derivative, a procyanidin or a procyanidin derivative, proanthrocyanidin, anthocyanins, quercetin, (+)-catechin, (−)-epicatechin, nobotanin, epigallocatechin gallate, gallotannins, hydroxytyrosol (3,4-dihydroxy phenylethanol), oleuropein, prodelphinidin, a combination thereof, or a pharmaceutically acceptable salt thereof.

3. The leaky balloon of claim 1 wherein the phenolic compound comprises tannic acid or an analog of tannic acid, pentagalloylglucose or an analog of pentagalloylglucose, a combination thereof, or a pharmaceutically acceptable salt thereof.

4. The leaky balloon of claim 1 wherein the therapeutic composition comprises about 0.0001 w/v % and about 10 w/v % of the phenolic compound.

5. The leaky balloon of claim 1 wherein the phenolic compound stabilizes the elastin of the blood vessel through cross linking with the elastin protein.

6. The leaky balloon of claim 1 wherein the therapeutic composition further comprises a drug delivery vehicle comprising a sustained release drug delivery vehicle, a hydrogel, a perivascular drug delivery vehicle, an endovascular drug delivery vehicle, or a combination thereof.

7. The leaky balloon of claim 6 wherein the drug delivery vehicle comprises a hydrogel comprising glycosaminoglycans, polysaccharides, proteins, dextran, hyaluronic acid, chitin, heparin, collagen, elastin, keratin, albumin, polymers and copolymers of lactic acid, glycolic acid, carboxymethyl cellulose, polyacrylates, polymethacrylates, epoxides, silicones, polyols such as polypropylene glycol, polyvinyl alcohol and polyethylene glycol and their derivatives, alginates such as sodium alginate or crosslinked alginate gum, polycaprolactone, polyanhydride, pectin, gelatin, crosslinked proteins peptides and polysaccharides, or a combination thereof.

8. The leaky balloon of claim 6 wherein the therapeutic composition is encapsulated in a drug delivery vehicle.

9. The leaky balloon of claim 6 wherein the drug delivery vehicle is biodegradable.

10. A method of repairing aneurysm in a blood vessel of a living subject using the leaky balloon of claim 1, the method comprising,
    deploying the leaky balloon at the aneurysm in the blood vessel, and
    eluting the therapeutic composition from the leaky balloon to stabilize the blood vessel at the aneurysm.

11. The method of claim 10 further comprising treating the blood vessel before, during, or after the deployment of the leaky balloon with glutaraldehyde.

12. The method of claim 10 wherein the aneurysm is treated with the leaky balloon multiple times.

13. The method of claim 10 wherein the leaky balloon is deployed in the aneurysm for sufficient period of time to allow the phenolic compound to cross link the elastin of the blood vessel.

* * * * *

UNITED STATES PATENT AND TRADEMARK OFFICE
CERTIFICATE OF CORRECTION

| | | |
|---|---|---|
| PATENT NO. | : 8,100,961 B2 | Page 1 of 1 |
| APPLICATION NO. | : 12/748849 | |
| DATED | : January 24, 2012 | |
| INVENTOR(S) | : Narendra R. Vyavahare, Jason C. Isenburg and Dan T. Simionescu | |

It is certified that error appears in the above-identified patent and that said Letters Patent is hereby corrected as shown below:

In the specification

Col. 1, lines 19-21 delete "The United States Government may have rights to this invention pursuant to National Institutes of Health Grant No. HL-61652." and replace with –This invention was made with government support under Grant #HL061652 awarded by the National Institutes of Health. The government has certain rights in the invention.–

Signed and Sealed this
Fifth Day of January, 2016

Michelle K. Lee
*Director of the United States Patent and Trademark Office*